US00PP10616P

United States Patent [19]

Walden

[11] Patent Number: Plant 10,616

[45] Date of Patent: Sep. 29, 1998

[54] SHRUB ROSE PLANT NAMED 'JACCHARI'

[75] Inventor: John K. Walden, Thousand Oaks, Calif.

[73] Assignee: Bear Creek Gardens, Inc., Medford, Oreg.

[21] Appl. No.: 768,858

[22] Filed: Dec. 17, 1996

[51] Int. Cl.[6] ..... A01H 5/00

[52] U.S. Cl. ..... Plt./1

[58] Field of Search ..... Plt./1, 7.1, 22, Plt./10, 28

*Primary Examiner*—Howard J. Locker

*Attorney, Agent, or Firm*—Klarquist Sparkman Campbell Leigh & Whinston, LLP

[57] ABSTRACT

A new and distinct variety of shrub rose plant having the unique combination of small, five-petaled, bright, deep-pink flowers born in large clusters; dark green, glossy foliage; arching and mounding growth habit; disease resistance, and rapid repeat flowering.

1 Drawing Sheet

The present invention relates to a new and distinct variety of rose plant of the shrub class which was originated by me by crossing the variety MORchari, U.S. Plant Pat. No. 5,975, with an unnamed seedling.

The primary objective of this breeding was to produce a new rose variety having the fragrance, plant habit and blooming habit of the female, combined with flower form, plant habit, bloom habit and disease resistance of the male, pink flowered, five-petaled parent. Except for not having any fragrance, the objective was substantially achieved, along with other desirable improvements, as evidenced by the following unique combination of characteristics that are outstanding in the new variety and that distinguish it from its parents, as well as from all other varieties of which I am aware:

1. Small, five-petaled, deep bright pink flowers borne in large clusters.
2. Dark green, glossy foliage.
3. Resistance to powdery mildew; tolerance of blackspot.
4. Rapid repeat flowering.
5. Arching and mounding growth habit.

Asexual reproduction of this new variety by softwood cutting, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—MORchari, U.S. Plant Pat. 5,975.

*Pollen parent.*—Unnamed seedling.

Classification:

*Botanical.*—*Rosa hybrida.*

*Commercial.*—Shrub.

FLOWER

Observations made from specimens grown in a garden environment at Wasco and Somis, Calif. in March–November, 1996.

Blooming habit: Recurrent, continuous, spring and fall.

Bud:

*Size.*—⅜-inch to ½-inch long when the petals start to unfurl.

*Form.*—The bud form is short, pointed ovoid.

*Color.*—When sepals first divide, bud color is Red-Purple Group 59B. When half blown, the upper sides of the petals are Red-Purple Group 61A; and the lower sides of the petals are Red-Purple Group 59B.

*Sepals.*—Color: Yellow-Green Group 144B. Surface texture: Slightly rough with small glandular structures of reddish color, Greyed-Purple Group 185A. There are three normally appendaged sepals. There are two unappendaged sepals with hairy edges.

*Receptacle.*—Color: Yellow-Green Group 146D. Shape: Apple. Size: Broad, small (3/16-inch to ¼-inch). Surface: Glandular, glands are Greyed-Purple Group 185A.

*Peduncle.*—Length: Short (½-inch to ¾-inch) . Surface: Glandular. Color: Light Green, bronzy. Strength: Stiff, erect, slender.

*Opening.*—Opens quickly to a flat to slightly-wavy flower.

Bloom:

*Size.*—Small. Average open size is 1¼ to 1⅜ inches.

*Borne.*—In flat clusters of 5–35 buds.

*Stems.*—Medium, strong. Average length is about 14–18 inches.

*Form.*—When first open: Flat. Permanence: Retains its form to the end.

*Petalage.*—Number of petals under normal conditions: 5.

*Color.*—The upper sides of the petals are Red Group 53D. The reverse sides of the petals are Red-Purple Group 59D. The base of each petal has a ⅛-inch crescent, Yellow-Green Group 150C in color, which fades to white. The major color on the upper sides is Red Group 53D.

*Variegations.*—None.

*Discoloration.*—The general tonality at the end of the first day: No change. At the end of the third day: Very slight lightening of color to Red-Purple Group 64C and very slight loss of vibrance.

*Fragrance.*—None.

Petals:

*Texture.*—Leathery.

*Shape*.—Round.

*Form*.—Flat to slightly ruffled.

*Arrangement*.—Imbricated, with no petaloids in the center.

*Persistence*.—Drop off cleanly.

*Lastingness*.—On the plant: Long (7–8 days). As a cut flower: Fair (5–7 days).

Reproductive parts:

*Anthers*.—Size: Small. Quantity: Many. Color: Yellow. Arrangement: Regular around styles.

*Filaments*.—Color: Yellow.

*Pollen*.—Color: Lemon Yellow.

*Styles*.—Color: Greenish White and Red.

*Stigmas*.—Color: Greenish White.

Plant:

*Form*.—Shrub.

*Growth*.—Very vigorous, sprawling with arching habit. Mature plant about 24-inches tall and 60-inches wide.

*Foliage*.—Number of leaflets on normal mid-stem leaves: 7.

*Size*.—Small (length 3¾"–4¼"; width 2"–2½").

*Quantity*.—Abundant.

*Color*.—New foliage: Both surfaces are initially Yellow-Green Group 144A with bronze tones of Greyed-Orange Group 171A. These colors change quickly (in 1–3 days) to the mature mid-stem leaf color (Green group 137A). Old foliage: Green Group 137A.

Leaflets:

*Shape*.—Pointed oval. *Texture*.—Upper side: Glossy. *Edge*.—Serrated.

*Serration*.—Single, small.

*Petiole Rachis*.—Color: New rachises are Yellow-Green Group 146B, tinted with Greyed-Red Group 178A which fades as plant ages.

*Petiole underside*.—With prickles.

*Stipules*.—Medium, bearded Yellow-Green Group 146A.

*Disease resistance*.—Resistant to mildew, blackspot and rust under normal growing conditions at Somis and Wasco, Calif.

Wood:

*New wood*.—Color: Yellow-Green Group 146B with tones of Greyed-Red Group 178B. In one to three days changes to Yellow-Green Group 146B. Bark: Smooth.

*Old wood*.—Color: Yellow-Green Group 146B. Bark: Smooth.

Prickles:

*Quantity*.—On main canes from base: Ordinary. On laterals from main canes: Ordinary.

*Form*.—Short (¼-inch), hooked downward.

*Color when Young*.—Red (Greyed-Red Group 178B). Shades towards amber as plant matures.

Small prickles: )

*Quantity*.—On main stalks: Few. On laterals: Few.

*Color*.—Brown, reddish (Red Group 46A) when young.

I claim:

1. A new and distinct variety of rose plant of the shrub class, substantially as herein shown and described, characterized particularly as to novelty by the unique combination of its small five-petaled, bright, deep-pink flowers born in large clusters; dark green, glossy foliage; arching and mounding growth habit; disease resistance; and rapid repeat flowering.

* * * * *

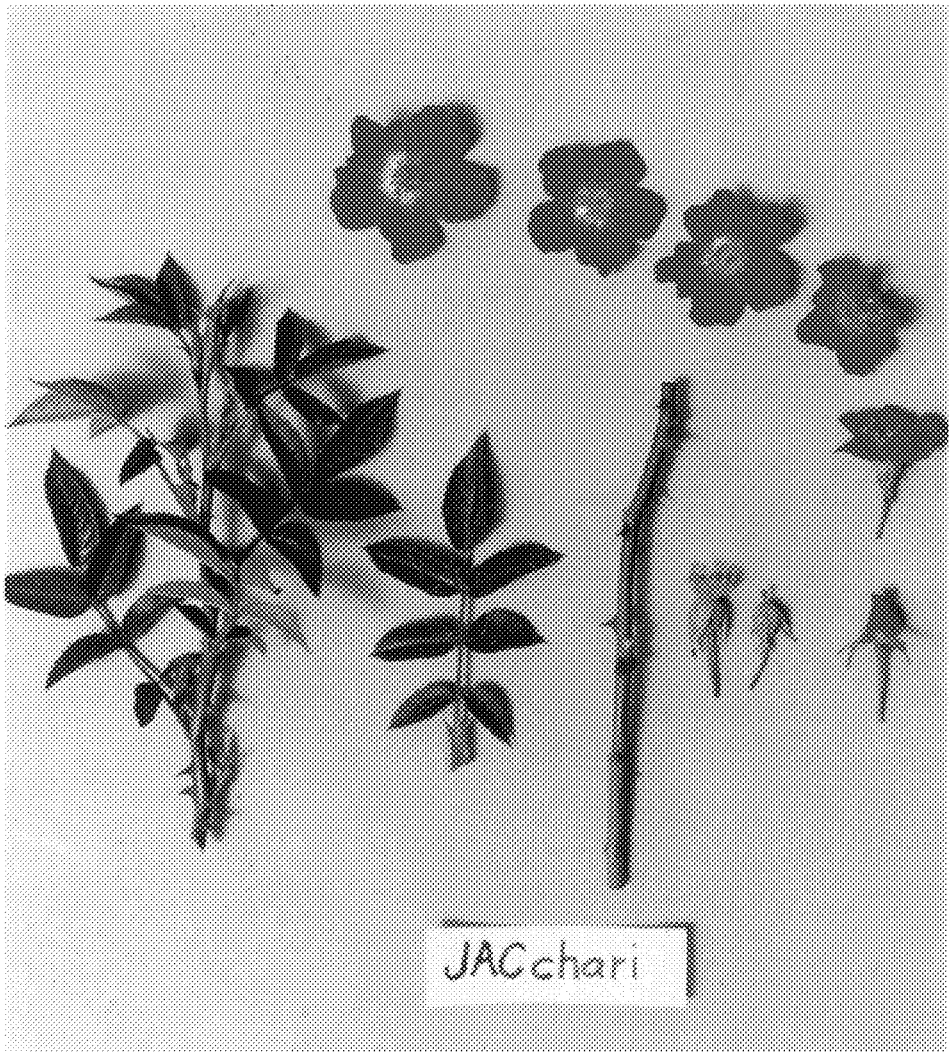
JACchari